US010512650B2

(12) United States Patent
Niichel

(10) Patent No.: US 10,512,650 B2
(45) Date of Patent: Dec. 24, 2019

(54) LAYERED SUSTAINED-RELEASE MICROBEADS AND METHODS OF MAKING THE SAME

(71) Applicant: Nano Pharmaceutical Laboratories LLC, Centennial, CO (US)

(72) Inventor: Robert Niichel, Greenwood Village, CO (US)

(73) Assignee: Nano Pharmaceutical Laboratories LLC, Centennial, CO (US)

( * ) Notice: Subject to any disclaimer, the term of this patent is extended or adjusted under 35 U.S.C. 154(b) by 0 days.

(21) Appl. No.: 15/899,715

(22) Filed: Feb. 20, 2018

(65) Prior Publication Data

US 2018/0369248 A1 Dec. 27, 2018

Related U.S. Application Data

(63) Continuation of application No. 14/732,574, filed on Jun. 5, 2015, now Pat. No. 9,931,344.

(60) Provisional application No. 62/102,477, filed on Jan. 12, 2015, provisional application No. 62/150,181, filed on Apr. 20, 2015.

(51) Int. Cl.
| | |
|---|---|
| A23P 10/30 | (2016.01) |
| A23P 10/35 | (2016.01) |
| A61K 31/4045 | (2006.01) |
| A61K 31/522 | (2006.01) |
| A61K 31/16 | (2006.01) |
| A61K 9/16 | (2006.01) |
| A61K 9/50 | (2006.01) |

(52) U.S. Cl.
CPC ............ *A61K 31/522* (2013.01); *A23P 10/30* (2016.08); *A23P 10/35* (2016.08); *A61K 9/167* (2013.01); *A61K 9/1652* (2013.01); *A61K 9/1676* (2013.01); *A61K 9/5015* (2013.01); *A61K 9/5031* (2013.01); *A61K 9/5047* (2013.01); *A61K 9/5073* (2013.01); *A61K 9/5078* (2013.01); *A61K 31/4045* (2013.01)

(58) Field of Classification Search
CPC .............. A61K 31/522; A61K 31/4045; A61K 9/1652; A61K 9/167; A61K 9/1676; A61K 9/5015; A61K 9/5031; A61K 9/5047; A61K 9/5073; A61K 9/5078; A23P 10/30; A23P 10/35
See application file for complete search history.

(56) References Cited

U.S. PATENT DOCUMENTS

| | | | |
|---|---|---|---|
| 4,182,778 A | 1/1980 | Hall et al. |
| 4,717,713 A | 1/1988 | Zatz et al. |
| 5,510,119 A | 4/1996 | Santus et al. |
| 5,558,879 A | 9/1996 | Chen et al. |
| 5,700,484 A | 12/1997 | Chauffard et al. |
| 5,728,403 A | 3/1998 | Mauger et al. |
| 6,001,392 A | 12/1999 | Wen et al. |
| 6,403,121 B1 * | 6/2002 | Adjei |
| 6,436,461 B1 | 8/2002 | Bouwmeesters et al. |
| 6,451,808 B1 * | 9/2002 | Cowles |
| 6,458,384 B2 | 10/2002 | Jaenicke et al. |
| 6,592,902 B2 | 7/2003 | Thosar et al. |
| 7,182,950 B2 | 2/2007 | Garti et al. |
| 7,915,247 B1 | 3/2011 | Arnold et al. |
| 8,545,892 B2 | 10/2013 | Niichel |
| 9,931,344 B2 | 4/2018 | Niichel |
| 2003/0077297 A1 | 4/2003 | Chen et al. |
| 2003/0148992 A1 | 8/2003 | Block et al. |
| 2004/0109894 A1 | 6/2004 | Shefer et al. |
| 2004/0234597 A1 | 11/2004 | Shefer et al. |
| 2005/0181041 A1 | 8/2005 | Goldman |
| 2006/0019098 A1 | 1/2006 | Chan et al. |
| 2006/0068019 A1 | 3/2006 | Dalziel et al. |
| 2006/0286259 A1 | 5/2006 | Hargreaves |
| 2006/0263427 A1 | 11/2006 | Roberts et al. |
| 2007/0148211 A1 * | 6/2007 | Altreuter |
| 2007/0238762 A1 | 10/2007 | Lautt |
| 2008/0075784 A1 | 3/2008 | Friesen et al. |
| 2008/0107789 A1 | 5/2008 | Akimoto |
| 2008/0213349 A1 | 9/2008 | Thakker et al. |
| 2009/0291137 A1 | 11/2009 | Guimberteau et al. |
| 2011/0064803 A1 | 3/2011 | Devane et al. |
| 2011/0195049 A1 | 8/2011 | Deftereos et al. |
| 2011/0229562 A1 | 9/2011 | Bar et al. |
| 2012/0034302 A1 | 2/2012 | Yu et al. |

FOREIGN PATENT DOCUMENTS

| | | |
|---|---|---|
| WO | 8303061 A1 | 9/1983 |
| WO | 2014079922 A1 | 5/2014 |

OTHER PUBLICATIONS

Ortiz (Pain Res Manag vol. 18, No. 5, published 2013, pp. 253-258) (Year: 2013).*
Canadian Pharmacy Shop (http://metformmwithoutprescription.ore, accessed Jun. 19, 2017, pp. 1-2) (Year: 2017).*
Cunningham and Cunningham (http://www.cunninghamlivestock.com/pioglitazone-iersey-use-no-prescription-pioglitazone-category-pioglitazone/, accessed May 29, 2017, pp. 1-2) (Year: 2017).*
International Pharmacies (http://www.consumerchoice-network.com/heaith/diabetes-2.him. Accessed Jul. 23, 2017, pp. 1-4) (Year: 2017).*
"Buy Zofran without Prescription" (http://getmedsonline.Org/zofran/#.WXTLFE3rvDA, accessed Jul. 23, 2017, pp. 1-2). (Year: 2017).*

(Continued)

*Primary Examiner* — Alma Pipic
(74) *Attorney, Agent, or Firm* — Perkins Coie LLP

(57) ABSTRACT

A layered microbead suitable for incorporating into a non-prescription consumable product is disclosed. The layered microbead may include a core and at least one active ingredient layer encapsulating the core. The active ingredient in the core can be different from the active ingredient in the encapsulating layer. The active ingredient in the core can be selected to counteract or enhance the effect of the active ingredient in the encapsulating layer. The layered microbead can further incorporate microspheres of active ingredient surrounded by polymer material. Method of manufacturing microspheres and microbeads are also described.

19 Claims, 8 Drawing Sheets

(56) References Cited

OTHER PUBLICATIONS

International Search Report and the Written Opinion of the International Searching Authority for PCT/US2015/034571, issued by the Korean Intellectual Property Office dated Oct. 28, 2015, 15 pages.
Park, J.H. et al., "Biodegradable polymers for microencapsulation of drugs," Molecules, 2005, vol. 10, No. 1, pp. 146-161.
"Caffeine," Wikipedia, retrieved online on Nov. 27, 2012, (p. 1-20).
"Theophylline," Wikipedia, retrieved online on Nov. 21, 2012, pp. 1-5.
Ballantyne, "Strange but true: drinking too much water can kill," Scientific American, Jun. 21, 2007, 29, p. 1-2.
Fox et al., "When caffeine kills: energy drinks under the spotlight," MSNBC, Oct. 23, 2012, (p. 1-6).
Kerrigan et al., "Fatal caffeine overdose: two case reportsm" Forensic Science International, 153 (2005), p. 67-69.

* cited by examiner

100C

LAYERED SUSTAINED-RELEASE MICROBEADS AND METHODS OF MAKING THE SAME

CROSS-REFERENCE TO RELATED APPLICATIONS INCORPORATED BY REFERENCE

This application is a continuation of U.S. patent application Ser. No. 14/732,574 filed Jun. 5, 2015, now issued as U.S. Pat. No. 9,931,344, which claims priority to and the benefit of U.S. Provisional Patent Application No. 62/102,477 filed Jan. 12, 2015, and U.S. Provisional Patent Application No. 62/150,181 filed Apr. 20, 2015. The foregoing applications are incorporated herein by reference in their entirety. To the extent the foregoing applications or any other material incorporated herein by reference conflicts with the present disclosure, the present disclosure controls.

BACKGROUND

Individuals taking supplements and/or medications are often required to ingest capsules, pills, tablets, or the like, multiple times per week, and in some instances, multiple times per day, in order to receive the necessary amount of active ingredients contained therein at the appropriate time. Traditionally, this requires individuals to self-monitor their supplement/medicine in-take, as through the use of a medication log or pill box having multiple labeled compartments. These methods provide ample opportunity for human error. Additionally, the requirement of having to take multiple pills per day or per week can be cumbersome and inconvenient. Further still, many individuals have difficulty taking medicine or supplements in the form of capsules, pills, tablets, and the like, due to their difficulty in swallowing such items.

To solve some of these problems, medications and/or supplements have been provided in sustained-release tablets, pills, or capsules. Sustained-release tablets, pills, or capsules attempt to alleviate the burdens of taking numerous pills, tablets or capsules per day by providing relatively large amounts of medicine in a single pill that gradually releases the active ingredient over an extended period of time once ingested. However, shortcomings of these sustained-release pills, capsules, or tablets can include a limited time period during which active ingredients are released (e.g., over 8 hours or less), a large size that is difficult to swallow, the delivery of only a single type of active ingredient, and the inability to provide finer tuned delivery of numerous active ingredients, including, e.g., desired time gaps between the delivery of active ingredients.

SUMMARY

This Summary is provided to introduce a selection of concepts in simplified form that are further described below in the Detailed Description. This Summary, and the foregoing background, is not intended to identify key aspects or essential aspects of the claimed subject matter. Moreover, this Summary is not intended for use as an aid in determining the scope of the claimed subject matter.

In some embodiments, a layered microbead is disclosed. The layered microbead can include a core and at least one active ingredient layer encapsulating the core. The core can include a plurality of microspheres intimately mixed together with binding agent such that binding agent and microspheres are located throughout the core. The microspheres can include at least one active ingredient and a polymer material encapsulating the at least one active ingredient. The at least one active ingredient layer can include at least one active ingredient and a binding agent. In some embodiments, the active ingredient in the microspheres is a different active ingredient from the active ingredient included in the active ingredient layer. In some embodiments, the active ingredient in the core is one which either counters or enhances the effects of the active ingredient in the active ingredient layer. In some embodiments, the layered microbead is a non-prescription microbead.

In some embodiments, a non-prescription consumable product is disclosed. The consumable product may have incorporated therein a layered microbead. The layered microbead may include a core and an active ingredient layer encapsulating the core. An active ingredient may be present in both the core and the active ingredient layer. In some embodiments, the active ingredient in the core is a different active ingredient from the active ingredient in the active ingredient layer. In some embodiments, the active ingredient in the core is one which either counters or enhances the effects of the active ingredient in the active ingredient layer.

In some embodiments, a method of manufacturing a layered microbead is disclosed. The method can include a step of mixing at least one active ingredient with at least one polymer to form a mass. The method can further include a step of micronizing the mass to form microspheres. The microspheres may be active ingredient encapsulated by the polymer. The method can further include a step of forming a microbead core and/or a microbead active ingredient layer incorporating the microspheres.

BRIEF DESCRIPTION OF THE DRAWINGS

Non-limiting and non-exhaustive embodiments of the methods and systems disclosed herein are described with reference to the following Figures, wherein like reference numerals refer to like parts throughout the various views unless otherwise specified.

DETAILED DESCRIPTION

Figure 1:
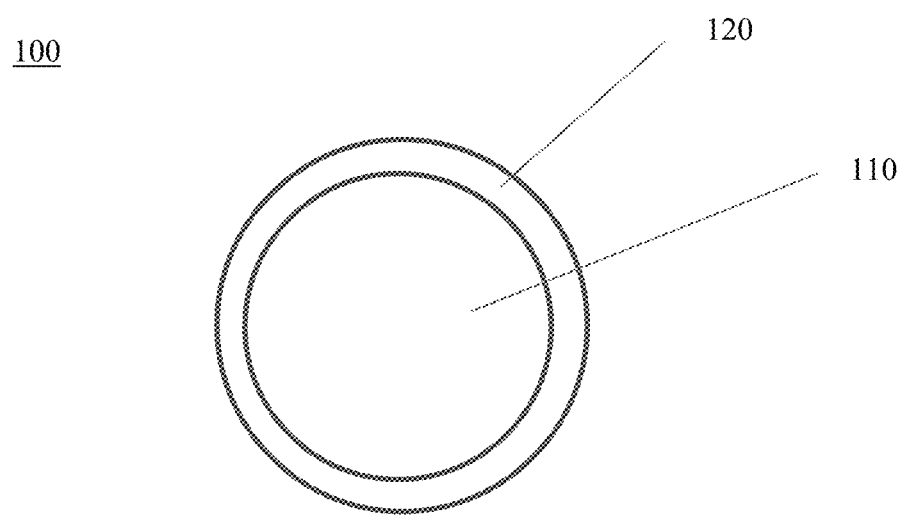
FIG. 1 is a cross sectional diagrammatic view of a layered microbead according to various embodiments described herein.

With reference to FIG. 1, a layered microbead 100 according to various embodiments described herein includes a microbead core 110 and at least one active ingredient layer 120 encapsulating the microbead core 110. At least one active ingredient is generally present in each of the microbead core 110 and the at least one active ingredient layer 120.

The microbead 100 is generally designed such that, once ingested by a consumer, the active ingredient in the active ingredient layer 120 is partially or fully released into the GI tract of the consumer prior to the release of the active ingredient in the microbead core 110. In this manner, the disclosed microbead is capable of providing both sustained and sequential release of active ingredients to a consumer.

The microbead 100 is generally spherical in shape, although other shapes can also be provided. In some embodiments, the diameter of the microbead 100 is in the range of from 1 to 5000 microns. The microbeads 100 are designed to be in this range such that the presence of the microbeads is generally masked when a consumer ingests the microbeads, including when the microbeads are incorporated into a food or drinkable consumer beverage product.

Generally speaking, the microbeads described herein are considered to be different from a capsule or tablet for several reasons. For example, the size of microbeads are smaller than tablets and capsules, making them generally easier to ingest. In some embodiments, the microbeads described herein have a size in the range of from 1 to 5,000 microns, while tablets and capsules are significantly bigger (e.g., 5,000 to 10,000 microns). Because microbeads are smaller than tablets and capsules, it becomes easier to incorporate multiple microbeads, including micobeads having different active ingredients, into a single consumable product, such as a food or beverage product. In contrast, large capsules and tablets are difficult to incorporate into a food or beverage.

The microbead core 110 can generally have a spherical shape and serves as the innermost portion of the microbead 100. The size of the microbead core 110 is generally not limited, though in some embodiments, the microbead core 110 has a diameter in the range of from 1 to 5,000 microns. The size of the microbead core 110 is generally kept relatively small such that the overall size of the microbead 100 is minimized. A microbead 100 having a relatively small size is generally desired such that the microbeads 100 can be incorporated into a food or drinkable consumer beverage and be consumed by a consumer without the consumer generally feeling the microbeads during ingestion.

In some embodiments, the microbead core 110 includes one or more active ingredients. In some embodiments, the microbead core 110 is made of exclusively active ingredients, while in other embodiments, the microbead core 110 can include active ingredients and other components. In one example, the microbead core 110 can include one or more active ingredients and one or more binding agents. The active ingredients, and binding agents can be intimately mixed so that both components are present throughout the core 110.

The binding agents can be used to help maintain the shape and stability of the microbead core 110 and/or control the rate at which the microbead core 110 breaks down once the microbead core 110 is exposed to the GI tract of the consumer. Any binding agent capable of providing stability to the microbead core 110 can be used and any combination of binding agents can be used. Exemplary binding agents suitable for use in the microbead core 110 include, but are not limited to methyl cellulose, ethyl cellulose, microcrystalline cellulose, croscarmellose sodium, dicalcium phosphate, cellulose, hypromellose, hydroxypropyl methylcellulose, carboxymethylcellulose, hydroxyethyl cellulose, povidone, polylactic acid, hypromellose, lipids/waxes, triglycerides, phospholipids, carnuba wax, cottonseed oil, palm oil, soybean oil, and stearines.

In some embodiments, the microbead core can further include one or more ion exchange resins. Ion exchange resins can provide stability to the microbead core by altering characteristics of the active ingredient in a manner that makes the active ingredient better suited for incorporation into the core. In some embodiments, the ion exchange resin is used to change the polarity, charge level, and/or solubility of the active ingredient to thereby stabilize the active ingredient in the core. Any suitable ion exchange resins can be used in any combination. Exemplary ion exchange resins include, but are not limited, Amberlite Pharmaceutical Grade Cation and Anion Exchange resins manufactured by Rohm-Haas.

In some embodiments, the microbead core can further include one or more complexing agents. Complexing resins and agents can provide stability to the microbead core by altering characteristics of the active ingredient in a manner that makes the active ingredient better suited for incorporation into the core. In some embodiments, the complexing agent is used to change the polarity, charge level, and/or solubility of the active ingredient to thereby stabilize the active ingredient in the core. Any suitable complexing agents can be used in any combination. Exemplary complexing agents include, but are not limited to, cyclodextrins, sodium chloride, potassium chloride, magnesium chloride, and calcium chloride, tannins, monocarboxylic acid, dicarboxylic acid, multi-carboxylic acid, 1-hydroxy 2-naphthoic acid, adipic acid, benzoic acid derivatives, caffeic acid, ellagic acid, ethyl gallate acid, gestistic acid, glutamic acid, glutaric acid, maleic acid, malonic acid, oxalic acid, succinic acid, and combinations thereof.

In some embodiments, the microbead core can further include one or more polymers. Polymers can provide stability to the microbead core by altering characteristics of the active ingredient in a manner that makes the active ingredient better suited for incorporation into the core. In some embodiments, the polymer is used to change the polarity, charge level, and/or solubility of the active ingredient to thereby stabilize the active ingredient in the core. Any suitable polymers can be used in any combination. Exemplary polymers include, but are not limited to, methyl cellulose, ethyl cellulose, microcrystalline cellulose, croscarmellose sodium, dicalcium phosphate, cellulose, prolamine protein (Zein), hypromellose, polylactic acid, hydroxypropyl methylcellulose, carboxymethylcellulose, hydroxyethyl cellulose, povidone, hypromellose, lipids/waxes, triglycerides, phospholipids, carnuba wax, cottonseed oil, palm oil, soybean oil, and stearines.

In some embodiments, the microbead core can further include one or more carrier agents. Carrier agents can provide stability and flowability in the manufacturing process and to the final microbead core by altering characteristics of the active ingredient in a manner that makes the active ingredient better suited for incorporation into the core. In some embodiments, the carrier agent is used to change the polarity, charge level, and/or solubility of the active ingredient to thereby stabilize the active ingredient in the core. Any suitable carrier agents can be used in any combination. Exemplary carrier agents include, but are not limited to, water, propylene glycol, Dibutyl sebacate, sunflower oil, oleic oil, corn oil, palm oil, coconut oil, palm kernel oil, rapeseed oil, cocoanut butter oil, soybean, cottonseed, omega oil, olive oil, carnuba palm oil, migloyl oil, vegetable oil, and hydrogenated versions of listed oils.

When a microbead core 110 includes both active ingredients and binding agent, the microbead core 110 can include from 5 to 95 wt % active ingredient and from 5 to 95 wt % binding agent (based on the total weight of the microbead core). In some embodiments, the 5 to 95 wt % binding agent includes the ion exchange resins, complexing agents, and/or polymers used in the cores.

Other components can also be included in the microbead core 110 to provide additional desired effects. Additional components that may be included in the microbead core 110 include, but are not limited to, pH balancers, fillers, and excipients. These components can be present in the microbead core 110 in any amount necessary to provide the desired effect.

The active ingredient layer 120 generally encapsulates the microbead core 110 such that the microbead core 110 can only be accessed by breaching the active ingredient layer 120. As shown in FIG. 1, the active ingredient layer 120 can have a uniform thickness, though active ingredient layers having non-uniform thickness are also possible. The thickness of the active ingredient layer 120 is generally not limited and can be varied based on a variety of different factors, including, for example, the amount of active ingredient to be provided in the active ingredient layer and the rate at which the active ingredient layer is desired to break down. In some embodiments, the active ingredient layer 120 has a thickness in the range of 10 to 2,500 microns.

The active ingredient layer 120 generally includes one or more active ingredients. In some embodiments, the active ingredient layer 120 is made of exclusively active ingredients, while in other embodiments, the active ingredient layer 120 can include active ingredients and other components. In one example, the active ingredient layer 120 can include one or more active ingredients and one or more binding agents. The active ingredient and binding agent can be intimately mixed so that both components are present throughout the core 110.

The binding agents can be used to help maintain the shape and stability of the active ingredient layer 120. The binding agent can also be provided to vary the rate at which the active ingredient layer 120 breaks down once ingested by a consumer. Any binding agent capable of providing stability to the active ingredient layer 120 can be used and any combination of binding agents can be used. Exemplary binding agents suitable for use in the active ingredient layer 120 include, but are not limited to methyl cellulose, ethyl cellulose, microcrystalline cellulose, croscarmellose sodium, dicalcium phosphate, cellulose, hypromellose, hydroxypropyl methylcellulose, carboxymethylcellulose, hydroxyethyl cellulose, povidone, hypromellose, lipids/waxes, triglycerides, phospholipids, carnuba wax, cottonseed oil, palm oil, soybean oil, and stearines.

When an active ingredient layer 120 includes both active ingredients and binding agent, the active ingredient layer 120 can include from 5 to 95 wt % active ingredient and from 5 to 95 wt % binding agent (based on the total weight of the active ingredient layer). In some embodiments, the 5 to 95 wt % binding agent further includes ion exchange resins and/or complexing agents.

In some embodiments, the presence of binding agents in the active ingredient layer 120 helps to prevent the substantial breakdown of the microbeads prior to ingestion by a consumer, such as when the microbeads are incorporated into a food or drinkable consumer beverage product and housed in the food or drinkable consumer beverage product for a period of time. Accordingly, in some embodiments, the amount of binding agent included in the active ingredient layer is specifically selected to prevent the substantial breakdown of the microbeads in these environments.

The ion exchange resins, complexing agents, carrier agents, and/or polymers discussed above with respect to the microbead cores 110 can also be used in any combination in the active ingredient layer 120. As discussed in greater detail above, the ion exchange resin, complexing agents, carrier agents, and/or polymers can be used to, e.g., alter characteristics of the active ingredient component of the active ingredient layer and thereby stabilize the active ingredient layer.

Other components can also be included in the active ingredient layer 120 to provide additional desired effects, such as providing additional defense against the substantial breakdown of microbeads incorporated into a food or drinkable consumer beverage product. Additional components that may be included in the active ingredient layer 120 include, but are not limited to pH balancers, fillers, and excipients. These components can be present in the active ingredient layer 120 in any amount necessary to provide the desired effect.

Figure 1A:
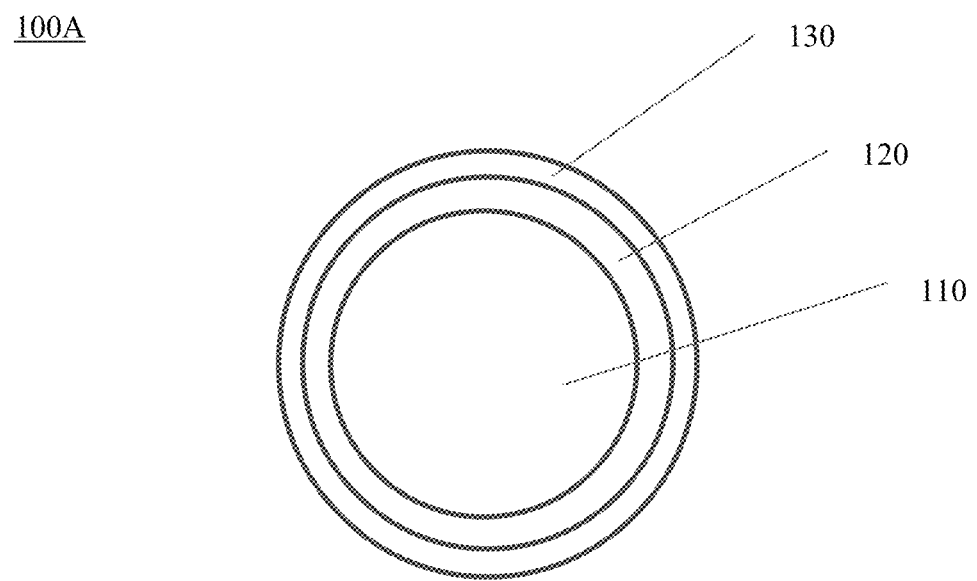
FIG. 1A is a cross sectional diagrammatic view of another layered microbead according to various embodiments described herein.

With reference to FIG. 1A, the disclosed layered microbead 100A can further include one or more exterior sealing layers 130. A sealing layer can generally be provided to ensure the layered microbead 100A can be stored for a period of time in a food or drinkable consumer beverage without the microbead substantially breaking down in the food or drinkable consumer beverage. Accordingly, the sealing layer 130 is preferably made from a material or combination of materials that will not substantially break down in a food or drinkable consumer beverage product but which will substantially break down in a consumer's GI tract. As used herein, the term substantially breakdown means that the microbead or component of the microbead fully deteriorates at a rate of less than 24 hours and, in some cases, in less than 8 hours. When the microbead or component of the microbead is designed to not substantially break down, this means that the microbead or component of the microbead does not fully deteriorate for at least a period of 24 hours and, in some cases for at least a period of days, weeks, months, or years. For example, when the microbeads are incorporated into a food or drinkable consumer beverage product that will then be sold to consumers at retails stores, it is necessary for the microbeads to not substantially break down for a sufficient period that provides the food or drinkable consumer beverage product with the necessary shelf life. In some embodiments, this shelf life needs to be several days, a week or more, a month or more, or more than 1 year. As a result, the microbeads and components of the microbeads should be capable of not substantially breaking down during the appropriate shelf life period.

In some embodiments, the sealing layer includes binding agents similar or identical to those optionally used in the microbead core and/or active ingredient layer. Exemplary components suitable for use in the sealing layer 130 include, but are not limited to alginate derivatives, trehalose (mylose), hydroxyectoine, o-toluidine, maltitol, lactitol, pamatinit, ectoine, polystyrene, polyvinylchloride, polycarbonate, polylactic acid polyethylene, mylar, cellophane, polyacrylates, ethylene-vinyl acetate polymers, non-erodible polyurethanes, polyvinyl fluoride, polyvinyl imidazole, chlorosulphonated polyolifns, polyethyleneoxide, polyvinyl alcohol, nylon, poly lactide, poly glycolic acid (PGA), polylactide-co-glycolide (PLGA), polycarbonates, Polycaprolactone, Polyamides, Polyanhydrides, Polyamino Acids, Polyorthoesters, Polyacetals, Polyhydroxyalkanoates, Polycyanoacrylates, Degradeable Polyurethanes, gums, latex, rubber, Cellulose Acetate Phthalate (Eastman-Cellacephate CAP), Vinyl Acetate Crotonic Acid Copolymer (Luviset), Methacrylic Acid/(Meth) Acrylic Acid Ester Copolymer (Eudragit), Hydroxypropyl Methylcellulose Phthalate, Polystyrene-Poly(Methylacrylate), Fillers/Plasticizers (such as CaCO3, Talc, TiO2, PEG, PVP), lipids and waxes, cottonseed, carnuba, olieic, soybean, palm, oleic, coconut, and hydrogenated versions of the listed above lipids and waxes, whey proteins, and combinations thereof.

The sealing layer 130 will generally encapsulate the microbead 100 such that the active ingredient layer 120 and the microbead core 110 cannot be accessed without breaching the sealing layer 130. As shown in FIG. 1A, the sealing layer 130 has a uniform thickness, although embodiments where the sealing layer has a non-uniform thickness are also envisioned. The sealing layer 130 can have any suitable thickness, and the specific thickness selected will often depend on the food or drinkable consumer beverage in which the microbeads may be deposited. For example, in food or drinkable consumer beverages having the ability to more quickly break down the sealing layer (e.g., acidic foods or drinkable consumer beverages), the thickness may be larger to prolong shelf life. In food or drinkable consumer beverages less capable of breaking down the sealing layer, the thickness may be smaller while still providing the desired shelf life. In some embodiments, the sealing layer has a thickness in the range of from 10 to 2,500 microns.

Figure 1B:
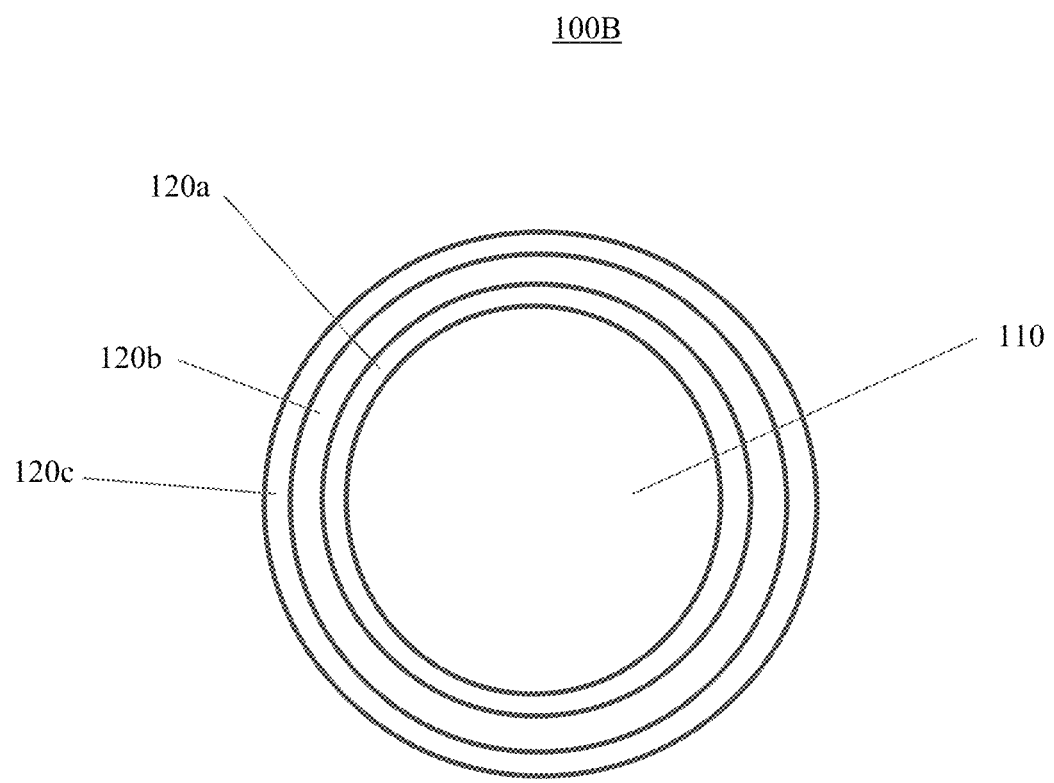
FIG. 1B is a cross sectional diagrammatic view of yet another layered microbead according to various embodiments described herein.

With reference to FIG. 1B, a microbead 100B having multiple active ingredient layers 120a, 120b, 120c is illustrated. While the microbead 100B shown in FIG. 1B shows a microbead 100B having three active ingredient layers 100, any number of active ingredient layers can be provided.

Each active ingredient layer 120a, 120b, 120c can be similar or identical to the active ingredient layer 120 described above in FIG. 1. Each active ingredient layer 120a, 120b, 120c can include one or more active ingredients and can also optionally include other components such as binding agents. The active ingredient layers 120a, 120b, 120c can all include the same active ingredients or one or more active ingredient layer can include different active ingredients from the other active ingredient layers. The active ingredient layers 120a, 120b, 120c, can all have identical thicknesses or one or more active ingredient layer can have a different thickness from the other active ingredient layers. The active ingredient layers 120a, 120b, 120c can all include binding agent, or only one or some of the active ingredient layers 120a, 120b, 120c can have binding agent. When the active ingredient layers 120a, 120b, 120c include binding agent, each layer can have an identical amount of binding agent or one or more active ingredient layer can have a different amount of binding agent from the other active ingredient layers.

In view of the above described variability possible in the active ingredient layers, the active ingredient layers 120a, 120b, 120c can each be specifically designed to provide a variety of desired effects. In one example, the amount of binding agent in an outer most active ingredient layer 120a can be lower than the other layers 120b, 120c such that, upon ingestion of the microbead, active ingredients in the layer 120a are quickly released into the GI tract of the consumer, while the active ingredients in the layers 120b and 120c are more slowly released into the GI tract. In another example, the amount of binding agent in an outer most active ingredient layer 120a can be higher than the other layers 120b, 120c such that, upon ingestion, the active ingredients in the layer 120a are released slowly, while the active ingredients in the layers 120b, 120c are released more quickly. This can provide for a situation where the microbead provides delayed release of the active ingredient, but normal continuous release of active ingredients once the initial delay is over.

While not shown in FIG. 1B, the microbead 100B can further include a sealing layer between some or all of the adjacent active ingredient layers (in addition to or alternative to the outer sealing layer 130 shown in FIG. 1A). The sealing layer provided between adjacent active ingredient layers can be similar or identical to the sealing layer 130 described above with respect to FIG. 1A. The presence of additional sealing layers between adjacent active ingredient layers can help to regulate the rate at which the active ingredients in each active ingredient layer are released into the GI tract of the consumer. A sealing layer located between active ingredient layers will generally result in a gap in time between when an active ingredient in an outer active ingredient layer is released and when an active ingredient in an inner active ingredient layer is released.

In some embodiments, one or more sealing layers are specifically provided between the microbead core and the active ingredient layer closest to the microbead core. Such a sealing layer can be similar or identical to the sealing layer 130 described above with respect to FIG. 1A. The sealing layer between the microbead core and the closest active ingredient layer can help to ensure that there is a period of time between the release of the active ingredient in the active ingredient layer closest to the microbead core and the release of the active ingredient in the microbead core. Such a delay can be useful in instances where, for example, the active ingredient in the microbead core is provided to counteract or reduce the effect of the active ingredients in the active ingredients layer (as will be discussed in greater detail below).

Figure 1C:
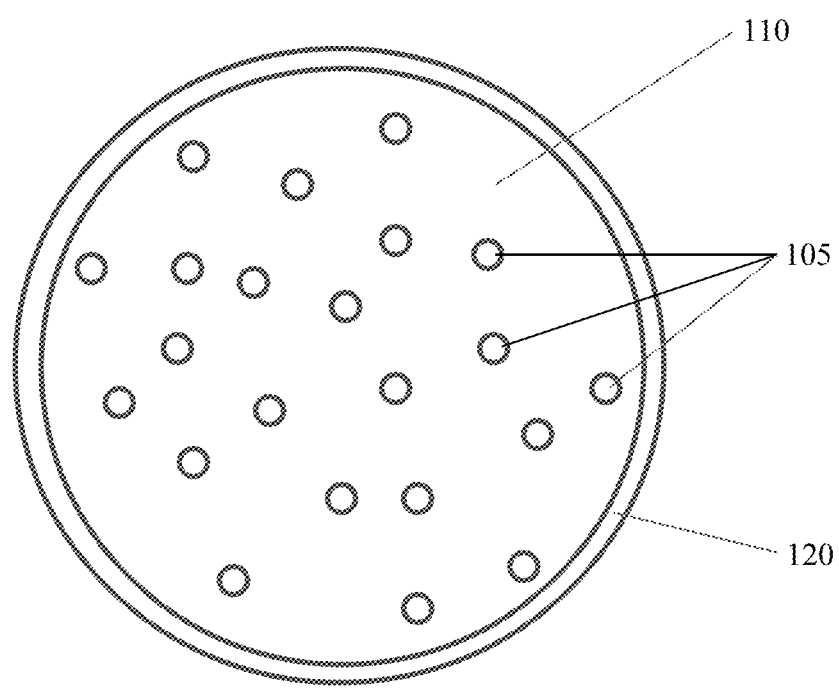
FIG. 1C is a cross sectional diagrammatic view of yet another layered microbead according to various embodiments described herein.

With reference to FIG. 1C, a microbead 100C can include a core 110 with active ingredient microspheres 105 distributed throughout the microbead core 110. Such a configuration allows for greater design options with respect to the rate and timing of active ingredient release. The microbead spheres 105 can also provide further stability and protection to the active ingredients located within the microbead spheres 105.

Each microsphere 105 can include one or more active ingredients coated with a sealing material. The core of the microspheres 105 can include exclusively active ingredient or can include other components, such as the binding agents, complexing agents, ion exchange resins, carrier agents, and/or polymers discussed in greater detail above. The sealing material coated around the active ingredient can fully encapsulate the active ingredient. In some embodiments, the sealing material of the microsphere is the polymer material described in greater detail above. In some embodiments, the size of the microspheres is in the range of from 0.001 to 2000 microns. Methods of forming the microspheres are discussed in greater detail below.

As shown in FIG. 1C, the microspheres are incorporated into a core 110. The core can be similar or identical to the cores 110 described in greater detail above. Accordingly, the core can include exclusively active ingredient, or a combination of active ingredient and binding agent or other components. In still other embodiments, the core material in which the microspheres 105 are incorporated is free of active ingredient and instead is made from binding agent and/or other components as discussed above. FIG. 1C also shows the core 110 being surrounded by an active ingredient layer 120, which is similar or identical to the active ingredient layer 120 described in greater detail above.

Figure 1D:
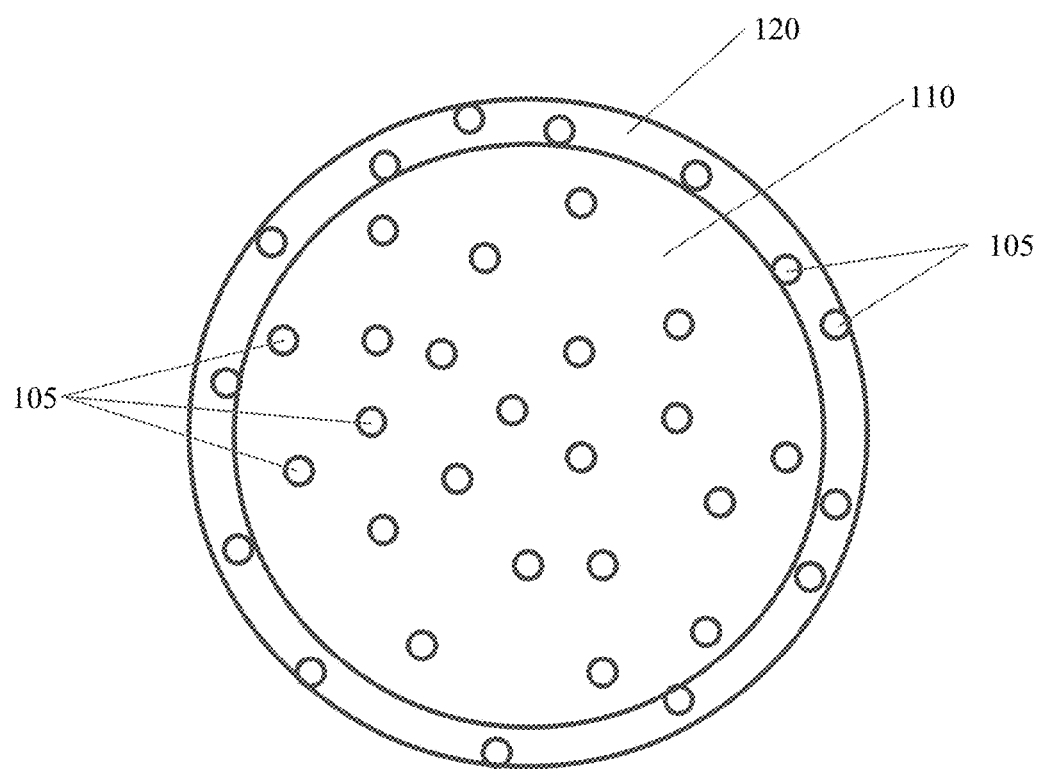
FIG. 1D is a cross sectional diagrammatic view of yet another layered microbead according to various embodiments described herein.

With reference to FIG. 1D, a microbead 100D is similar to the microbead 100C shown in FIG. 1C, with the exception that microspheres 105 are also incorporated into active ingredient layer 120. In such embodiments, the active ingredient layer in which the microspheres 105 are dispersed can also include active ingredients, or the active ingredient layer 120 can be free of active ingredient (in which case, the active ingredient would be more similar to the sealing layers described in greater detail above).

FIG. 1D shows a microbead 100D having a single active ingredient layer 120 with microspheres 105 disposed therein. However, the number of active ingredient layers 120 is not limited. Similarly, when multiple active ingredient layers 120 are provided one or more of the active ingredient layers may include microspheres 105, while other active ingredient layers may be free of microspheres 105. The active ingredients included in the various layers, cores, and microspheres can be the same active ingredient or any combination of different active ingredients.

In any of the embodiments described above, the microbead 100, 100A, 100B, 100C, 100D can be substantially or completely free of water. As used herein, the term substantially free means less than 2.5 wt % water present in the microbead (based on the total weight of the microbead). The absence of water in the microbeads can help to ensure that the microbeads do not substantially breakdown when incorporated into, e.g., a drinkable consumer beverage. Instead, the microbeads having little or no water will only begin to appreciably break down upon being exposed to the GI tract of a consumer.

The active ingredients that can be included in the mircobeads are generally not limited and may include any active ingredient that promotes or induces any type of effect or change in a human consumer.

Exemplary active ingredients include, but are not limited to, nutraceuticals, vitamins, supplements, minerals, enzymes, probiotics, bronchodilators, anabolic steroids, analeptics, analgesics, proteins, peptides, antibodies, vaccines, anesthetics, antacids, antihelmintics, anti-arrthymics, antibiotics, anticoagulants, anticolonergics, anticonvulsants, antidepressants, antidiabetics, antidiarrheals, anti-emetics, anti-epileptics, antihistamines, antihormones, antihypertensives, anti-inflammatories, antimuscarinics, antimycotics, antineoplastics, anti-obesity drugs, antiprotozoals, antipsychotics, antispasmotics, anti-thrombics, antithyroid drugs, antitussives, antivirals, anxiolytics, astringents, beta-adrenergic receptor blocking drugs, bile acids, bronchospasmolytic drugs, calcium channel blockers, cardiac glycosides, contraceptives, corticosteriods, diagnostics, digestives, probiotics, diuretics, dopaminergics, electrolytes, emetics, haemostatic drugs, hormones, hormone replacement therapy drugs, hypnotics, hypoglycemic drugs, immunosuppressants, impotence drugs, laxatives, lipid regulators, muscle relaxants, pain relievers, parasympathicolytics, parasympathicomimetics, prostagladins, psychostimulants, sedatives, sex steroids, spasmolytics, sulfonamides, sympathicolytics, sympathicomimetics, sympathomimetics, thyreomimetics, thyreostatic drugs, vasodialators, and xanthines; drugs or medicaments, breath fresheners, vitamins and other dietary supplements, minerals, caffeine, theacrine, cannabis, nicotine, fruit juices, and the like, and mixtures thereof. Examples of useful drugs include ace-inhibitors, antianginal drugs, anti-arrhythmias, anti-asthmatics, anticholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra™, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocryptine or nicotine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, cannabis, THC, CBD, and combinations thereof.

The active ingredients selected for use in the consumable can be used to address a variety of conditions. In some embodiments, the active ingredients are selected from those generally used to enhance physical performance, such as stimulants, electrolytes, vitamins, and minerals. In such embodiments, the consumable matrix can be used to deliver any of the active ingredients on demand and in response to a specific event in an athletic competition (e.g., an on demand release of caffeine at the beginning of a steep climb in a bicycle race). In some embodiments, the active ingredients can be medicine needed to treat and/or prevent a variety of conditions. In a specific example, the active ingredients are selected to treat life threatening conditions, such as in a human having a high risk for heart attacks, in which case the consumable can provide nitroglycerin on demand (and potentially by a remote user, such as a doctor, monitoring such a patient). In still another embodiment, the active ingredient can be any type of appetite suppressant such that the consumable can be used by individuals trying to lose weight. In such embodiments, the consumable can be used to deliver the appetite suppressant on demand, such as when the user feels a food craving.

The active ingredients can be included in the microbead in any desired quantity and in any desired combination. In some embodiments, the microbeads include two or more active ingredients that are specifically selected to work in concert to achieve some desired result. Different active ingredients can be located in different parts of the microbead for sequential release of active ingredients. In some embodiments, a first active ingredient is included in the one or more active ingredient layers and a second active ingredient different from the first active ingredient is included in the microbead core. In some embodiments, a first active ingredient is provided in one or more outer active ingredient layers, and a second active ingredient different from the first active ingredient is included in one or more inner active ingredients layers (i.e., active ingredient layers located closer to the microbead core than the outer active ingredient layers). In such embodiments, the microbead core can include the first active ingredient, the second active ingredient, a third active ingredient different from the first and second active ingredient, or a combination thereof. A microbead with multiple active ingredient layers can also include alternating layers of different active layers, such as a microbead with a first, third, and fifth active ingredient layer each including the same first active ingredient, and a second and fourth active ingredient layer each including the same second active ingredient that is different from the first active ingredient. Ultimately, and combination of active ingredient layers and active ingredients can be designed to carry out any of a range of desired effects.

In some embodiments, the microbead includes two or more active ingredients, wherein at least one of the active ingredients counteracts or reduces the effect of the one of the other active ingredients. Typically, the active ingredient without the counteracting or reducing effect will be located in one or more inner active ingredient layers and/or in the microbead core. In this manner, the microbead will release a first active ingredient from one or more outer active ingredient layers, followed by the release of a second active ingredient in the inner active ingredient layers and/or microbead core which counteracts or reduces the effect of the first active ingredient.

Any combination of active ingredients where the second active ingredient counteracts or reduces the effect of the first active ingredient can be used. Exemplary combinations include a sleep aid such as melatonin (to induce sleep) and a stimulant such as caffeine (to wake up an individual).

In some embodiments, the microbead includes two or more active ingredients, wherein the at least two active ingredients combine to provide a complimentary effect or wherein one active ingredient enhances the other active ingredient. This can include active ingredients that are traditionally given separately but in sequential order to obtain a desired effect. Typically, the active ingredient that is to be delivered first will be located in one or more outer active ingredient layers, while the active ingredient that is to be delivered second will be located in one or more inner active ingredient layers and/or in the microbead core. In this manner, the microbead will release the first active ingredient from one or more outer active ingredient layers, followed by the release of the second active ingredient in the inner active ingredient layers and/or microbead core which compliments or enhances the effect of the first active ingredient.

Any combination of active ingredients where the second active ingredient enhances or compliments the effect of the first active ingredient can be used.

In some embodiments, the microbeads are specifically formulated so that the microbeads are non-prescription and/or not subject to FDA regulation. This can include the use of exclusively non-prescription active ingredients, the use of prescription active ingredients in non-prescription quantities, the use of exclusively GRAS (Generally Regarded As Safe) components, the use of exclusively components that are used in GRAS compliant quantities, or combinations thereof. The term GRAS as used herein is intended to include components which are currently regarded as GRAS as well as components that may be regarded as GRAS in the future. In some embodiments, the disclosed microbeads are designed for over-the-counter sale, including when incorporated into food and drinkable consumer beverages.

As alluded to above, the microbeads described herein can be incorporated into a food or drinkable consumer beverage product such that an individual consumes a food or drinkable consumer beverage product in order to consume the microbeads. Any food or drinkable consumer beverage product can be used in conjunction with the microbeads. Food products can include, for example, baked goods, such as bars, breads, cookies, brownies, and the like. Other food products include cereals, oatmeal, yogurts, jellies, and other more fluid-type solids. Drinkable consumer beverage products can include, for example, water, juices, coffee, shakes, smoothies, energy drinks, sodas, and the like. The microbeads can also be incorporated into gummies and gels.

When incorporated into food or drinkable consumer beverage products, the microbeads are typically designed such that the microbeads do not substantially breakdown in the food or drinkable consumer beverage product for an extended period of time. This allows the products into which the microbeads are incorporated to have a sufficient shelf life needed for, for example, retail sale requirements. Any manner of preventing the microbeads from substantially breaking down in the food or drinkable consumer beverage product can be used, including, for example, providing sealing layers, additional amounts of binding agent, and the like, as discussed in greater detail above.

The microbeads can also be stored and/or sold in stick packets so that the microbeads can be added to a food or drinkable consumer beverage product at a later time. In one specific example, a stick packet is provided wherein the amount of microbeads stored therein is a specific quantity making the microbeads suitable for incorporation into a standard water bottle (e.g., a water bottle having 16.9 fluid ounces of water). In such embodiments, the microbeads stored in the stick packets may require fewer sealing layers or less binding agents since the microbeads are only added to the food or drinkable consumer beverage product upon the consumers intention to ingest the food or drinkable consumer beverage product.

Figure 2:
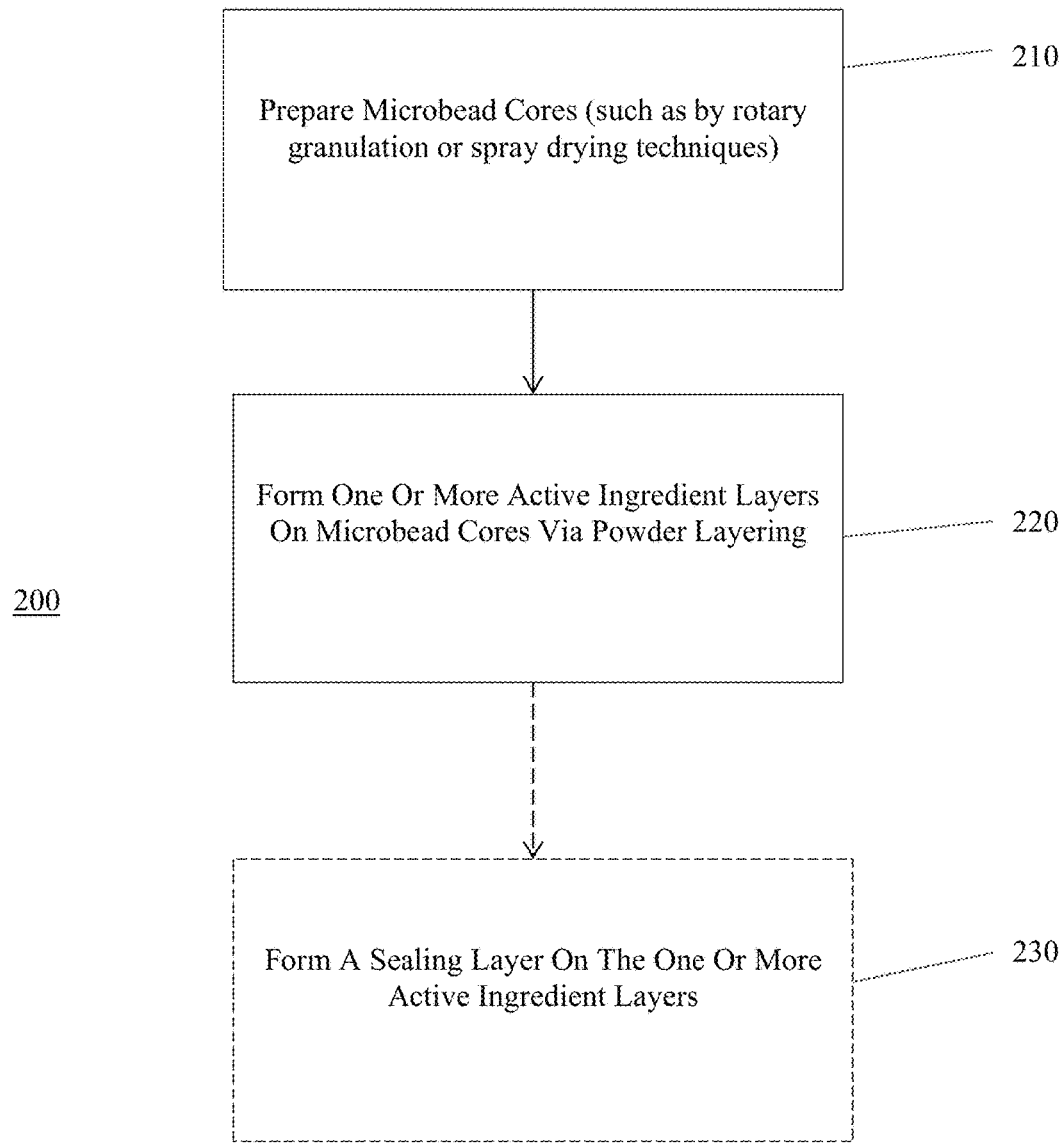
FIG. 2 is a flow diagram illustrating a method of forming layered microbeads according to various embodiments described herein.

With reference to FIG. 2, a method 200 of preparing the microbeads described herein can generally include the following steps: a step 210 of forming a microbead core, a step 220 of forming one or more active ingredient layers, such as via powder layering techniques, and an optional step 230 of forming a sealing layer.

Regarding step 210 of forming a microbead core, this step can include using any technique or method known for creating micron-scale, generally spherical cores that include at least an active ingredient. In some embodiments, the microbead core is formed using rotary granulation techniques, powder layering techniques, spray drying techniques, spray chilling techniques, liquid extrusion/coextrusion, 3-D Printing. concentric nozzles, extrusion/spheronization, and combinations thereof.

In the rotary granulation technique, a rotary granulator is generally employed, and any suitable rotary granulator capable of forming micron-scale cores can be used. The method of forming the microbead core generally includes depositing a dry powder into the rotary granulator, which is then blown airborne. Once airborne, a liquid is sprayed into the chamber of the rotary granulator. Agglomeration of the microbead cores occurs via coalescence. The process forms spherical-shaped cores of generally uniform size.

The dry powder mix deposited in the rotary granulator can include at least the one or more active ingredients to be present in the microbead core. The dry powder mix can include other optional components of the microbead core, as desired, such as the binding agent and other components discussed above. The amount of active ingredients and other components present in the dry powder mix can be similar or identical to the amounts discussed above.

The liquid sprayed into the rotary granulator can include at least the one or more binding agents to be present in the microbead core. In some embodiments, the rotary granulator produces a core that is an intimate mixture of active ingredient and binding agent (i.e., both the active ingredient and the binding agent are dispersed throughout the core). The amount of binding agent sprayed into the rotary granulator can be in accordance with the amounts described above with respect to the make-up of the core.

The size of the microbead cores formed in the rotatory granulator can be similar or identical to the size ranges discussed above. In some embodiments, the size of the microbead cores is in the range of from 50 to 500 microns. In some embodiments, the resulting micobead cores formed in the rotary granulator are dry and substantially free of water.

In the spray drying technique, formation of the microbead cores begins by preparing a solution or dispersion containing at least the one or more active ingredients to be included in the microbead core. The dispersion or solution is then atomized and sprayed into a chamber through a heated air stream. This causes the liquid component of the solution or dispersion to evaporate quickly, resulting in dried, generally spherical shaped microbead cores. The spray drying system may have two or three nozzles for the process.

The solution or dispersion can include one or more active ingredient as discussed in greater detail above. The dispersion can further include components such as binding agents, fillers, etc, as discussed in greater detail above. The amount of active ingredients and other components can be similar or identical to the amounts discussed above. In some embodiments, the spray drying technique can be used to produce a core that is only active ingredients. In other embodiments, the cores produced are intimate mixtures of binding agent, active ingredient, and other optional components.

The size of the microbeads formed by the spray drying technique can be similar or identical to the size ranges discussed above. In some embodiments, the size of the microbead cores is in the range of from 1 to 2000 microns. The microbead cores formed by this method can be substantially free of water.

In the spray chilling technique, the active ingredient and binding agent are mixed together in a heated pressurized container such that the system is brought into a molten state. The liquid resulting from this step is then sprayed (e.g., via an atomizer) into a cool stream. When the sprayed liquid contacts the cool stream, the droplets solidify and form particles. No solvent is needed in this process. The cores produced by the chilling technique can be intimate mixtures of active ingredients and binding agents.

In some embodiments, the microbead cores are formed using an encapsulator device. Exemplary encapsulator devices include, but are not limited to, the Buchi Encapsulator B-390 manufactured by Buchi Labortechnik AG of Flawil, Switzerland. Encapsulator devices generally include a nozzle through which a microbead core solution is passed to form a stream of droplets of the solution material. The size of the droplets can be adjusted using, e.g., vibration applied proximate the nozzle and the flow rate of the solution through the nozzle. In some embodiments, the nozzle is vertically oriented such that droplets leave the nozzle under the force of gravity and collect in a liquid bath positioned under the nozzle. When the droplets contact the liquid bath, microbead core formation occurs, such as solidification effected via cooling or heating of the droplets. Any suitable liquid bath can be used to collect the droplets, including, e.g., aqueous solutions containing cations with a 2+ charge (e.g., $Ca^{2+}$, $Cu^{2+}$, $Fe^{2+}$, $Sn^{2+}$, $Cr^{2+}$, $Mn^{2+}$, $Mg^{2+}$, $Zn^{2+}$, etc.) and organic solutions that perform a cooling function (e.g., ethanol, methanol, etc.).

Formation of hardened microbead cores can also be assisted by heating or cooling the air through which the stream of droplets travel prior to hitting the liquid bath. The cores formed in the liquid bath may have hydrophobic or hydrophilic characteristics. Once the cores are formed in the liquid bath, the cores can be collected and subjected to further processing steps, such as the active ingredient layer coating steps discussed below.

The microbead core solution that is pumped into and through the nozzle of the encapsulator device can generally include the one or more active ingredient to be included in the microbead core and any other material used to bind together the microbead core (e.g., carrier material, polymers, and binding agents). The amount of each component included in the solution is generally consistent with the ranges of material described above for the microbead cores. The different components of the microbead core solution are generally mixed together prior to being pumped to the nozzle. In some embodiments, the lines between the microbead core solution and the nozzle of the encapsulator device are heated lines to ensure that all of the components of the microbead core solution are suitably liquefied.

In the 3-D printing technique, formation of the microbead cores begins by preparing a dispersion or filament containing a polymer and/or at least the one or more active ingredients to be included in the microbead core. Multiple dispersions or filaments may be used containing polymers or one or more active ingredients, individually or in combination. The dispersion or filament is then printed in layers onto the base of the 3D printer in the form of a microbead core. The specific size and shape of the core can be selected and controlled by using different software programs run on the 3D printer. When the dispersion is a combination of polymer and active ingredient, the core formed by the 3D printing method can be an intimate mixture of polymer and active ingredient throughout the core.

Regarding step 220 of forming one or more active ingredient layers, the active ingredient layer can be formed by any suitable manner of forming a layer encapsulating the microbead core formed in step 210. Exemplary layering techniques include, but are not limited to, powder layering and 3D printing methods.

When powder layering is used, the powder layering generally includes spraying the one or more components of the active ingredient layer into a chamber that contains microbead cores. In some embodiments, both an active ingredient and a binding agent are sprayed into the chamber. The binding agent generally serves to saturate the microbead cores and interact with the active ingredient, which results in the formation of a layer of active ingredient on top of and encapsulating the microbead core.

In some embodiments, the powder layering is carried out in a rotary granulator. The binding agent and active ingredient can each be sprayed into the chamber using nozzles having a tangent nozzle position. When carried out in a rotary granulator, the layers are densified and spheronized via contact with the spinning rotor plate of the rotary granulator.

The powder layering step can be carried out multiple times, including with different active ingredients and/or binding agents, to form multiple active ingredient layers over the core.

In some embodiments, the layering step 220 is carried out using a 3-D printing technique. Formation of the layers begins by preparing a dispersion or filament containing a polymer and/or at least the one or more active ingredients to be included in the active ingredient layer. The dispersion or filament is then layered/printed on, over, and/or around the core formed in step 210. In some embodiments, a bottom portion of the active ingredient layer can be printed, followed by placing the core in the bottom portion of the active ingredient layer (e.g., such as by the core in a "nest" that is the bottom portion of the active ingredient layer), and subsequently printing the remaining portion of the active ingredient layer over, around and/or on top of the core to encapsulate the core. The printing of the active ingredient layers is carried out systematically utilizing the 3-D printing system and software. Multiple layers of active ingredient layers can be formed on a single core by repeating the 3D printing step.

In order to create multiple layers, the layering step 220 can be carried out multiple times with different and/or identical active ingredients and binding agents. For example, a first active ingredient layer can be formed on a microbead core according to any of the methods discussed above, followed by adding additional layers by any of the methods discussed above. In some embodiments where powder layering is used, the microbead cores formed in step 210 are coated with an active ingredient layer via powder layering in a rotary granulator. The layered microbead core is then left in the chamber. The active ingredient being sprayed into the chamber is then changed and the process is repeated, with the binding agent saturating the layered microbead and interacting with the second active ingredient to thereby form a second active ingredient layer. This process can be carried out any number of times with any number of active ingredients, including the use of identical active ingredients for multiple active ingredient layers.

Regarding optional step 230, a sealing layer (or sealing layers) can be formed on the microbead. In some embodiments, the sealing layer is formed as the outermost layer of the microbead. In some embodiments, the microbead includes multiple sealing layers, with some sealing layers being between adjacent active ingredient layers and/or between the microbead core and the inner-most active ingredient layer. These sealing layers generally serve to slow the release of active ingredients by preventing access to the layers containing the active ingredients. As discussed above, the outer most sealing layer can serve as a way of preventing the microbead from substantially breaking down prior to be consumed by an individual.

The sealing layer (or sealing layers) formed in step 230 can be similar or identical to the sealing layers discussed in greater detail above. Generally, the sealing layers formed in step 230 do not contain any active ingredients. Any manner of forming a sealing layer can be used. In some embodiments, the sealing layer is formed as part of a powder layering process. 3-D Printing techniques as discussed herein can also be used.

In some embodiments, a sealing layer can be formed on top of an active ingredient layer by continuing to spray binding agent into the chamber after spraying of active ingredient is stopped. The binding agent that is sprayed into the chamber without also spraying active ingredient into the chamber saturates the active ingredient layer and begins to accumulate on the surface of the microbead to thereby form a sealing layer that includes only binding agent. This process can be used to form sealing layers throughout the microbead.

In some embodiments, steps 210 and 220 can be performed simultaneously. For example, coextrusion and 3D printing methods can both be used to effectively carry out the formation of the microbead core and one or more surrounding layers at the same time.

Figure 3:
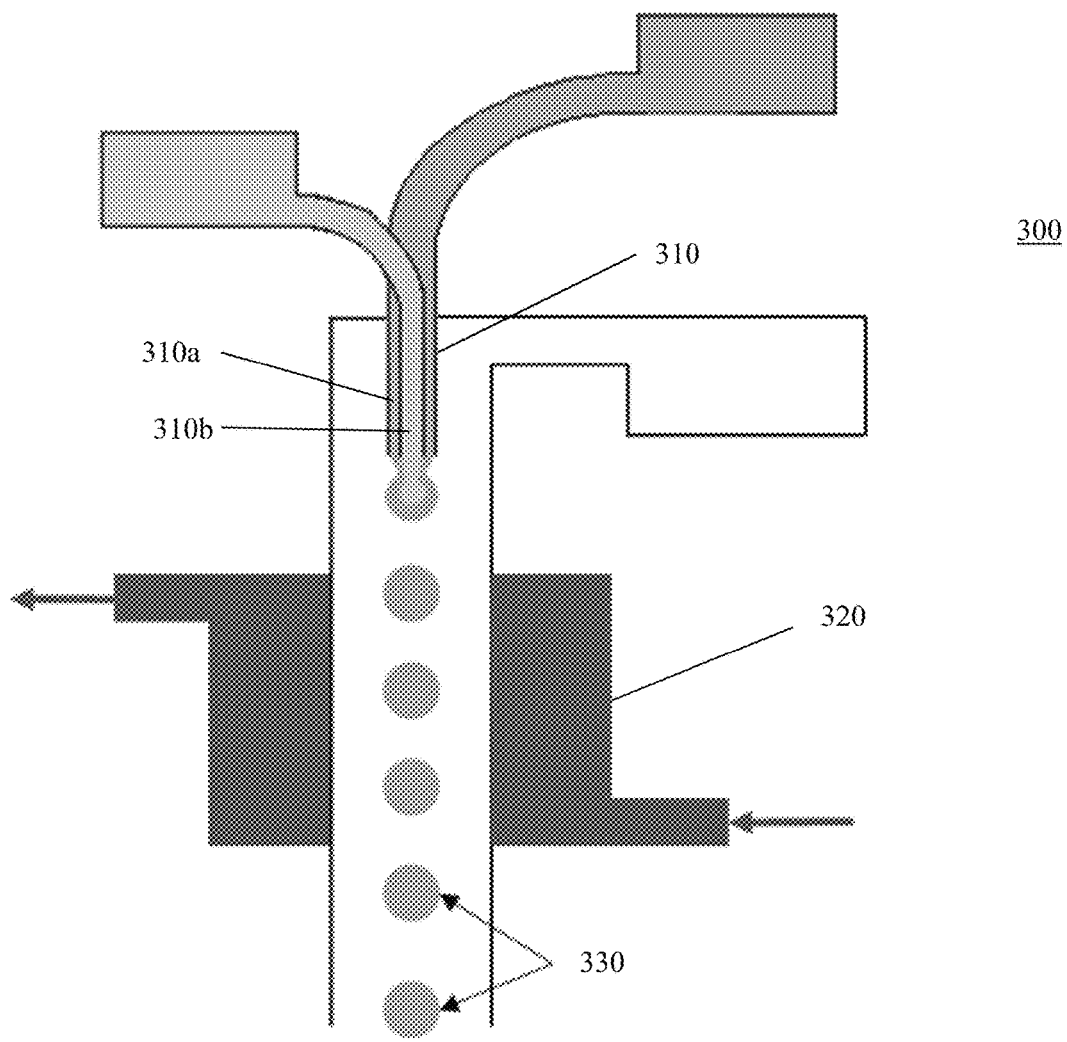
FIG. 3 is a simplified cross sectional illustration of an encapsulator device suitable for use in a co-extrusion process according to various embodiments described herein.

With reference to FIG. 3, the coextrusion method can generally include the use of an encapsulator device 300 as described above, but wherein the encapsulator device 300 is fitted with a concentric nozzle 310. The concentric nozzle 310 includes an inner passage 310a and an outer passage 310b aligned concentrically with the inner passage 310a. Material for the microbead core can be pumped through the inner passage 310a, while material for the encapsulating active ingredient layer can be pumped through the outer passage 310b. The terminal ends of the inner passage 310a and the outer passage 310b are aligned so that when material exits out of each passage, the active ingredient layer material encapsulates the microbead core material and forms a stream of layered droplets 330. As described previously, this stream of droplets 330 falls under the force of gravity into a liquid bath (not shown) which serves to collect the droplets 330 and harden the droplets 300 so that layered beads are formed.

The solution for the core can be similar or identical to the solution described above with respect to step 220 of method 200. For the coextrusion process, a solution of active ingredient layer is also provided and pumped to the nozzle. The solution for the active ingredient layer generally includes the one or more active ingredient to be included in the active ingredient layer and any other material used to in the active ingredient layer (e.g., polymers, lipids, waxes, proteins, gums, and/or binding agents). The amount of each component included in the solution is generally consistent with the ranges of material described above for the active ingredient layers. The active ingredient layer solution can be The shell material may be at ambient temperature or heated to temperatures adequate to liquefy the components. The shell material may have hydrophobic or hydrophilic characteristics.

Features of the encapsulator device 310 can generally be similar or identical to the encapsulator device and methods described above with respect to step 220 of method 200. For example, the encapsulator device can be a Buchi Encapsulator B-390 and can include heated lines to ensure the solution material being pumped to the nozzle is sufficiently liquidized. Vibration and flow rates can also be adjusted to adjust the size of the droplets.

While FIG. 3 illustrates an embodiment wherein the nozzle include an inner passage 310a and a single outer passage 310b, the nozzle can include additional concentrically aligned outer passages to provide additional layers to the bead, including additional active ingredient layers or sealing layers.

As with the encapsulator device described previously, the stream of layered droplets travel through air and are captured in a liquid basin. The air that the layered droplets travel through post-extrusion may be warmed or cooled (via, e.g., heat exchanger 320 shown in FIG. 3) to accelerate the formation/hardening process. The liquid in the liquid basin may include a hydrophilic based-polymer or organic system (i.e., 2+ ion systems, ethanol, methanol, etc). The liquid basin may be heated or cooled to accelerate the hardening process in the liquid.

3D printing techniques can also be used to carry out the simultaneous formation of the microbead core and one or more active ingredient layers and/or sealing layers. Such a method would generally entail the use of a 3D printer having multiple nozzles, with each nozzle depositing a different dispersion or filament. As discussed previously, the dispersion or filament can include any combination of ingredients needed for the micorbead core, the active ingredient layer, or the sealing layer. The 3D printer with multiple nozzles (running specific software designed for the specific printing of the microbead) is used to form a microbead having at least one active ingredient layer or sealing layer in a normal fashion, such as by a sequential layer on top of layer process. The specific size and shape of the layered microbead, including the size and shape of the core and the thickness of each layer encapsulating the core can be selected and controlled by using different software programs run on the 3D printer.

Still another optional step that can be included in the above-described method is the incorporation of the formed micro-beads into a food or drinkable consumer beverage product. The food or drinkable consumer beverage product is generally a non-pharmaceutical product. The food or drinkable consumer beverage product can also be a GRAS-compliant product.

Any manner of incorporating the micro-beads into a food or drinkable consumer beverage product is generally not limited. With respect to drinkable consumer beverage products (or viscous food products or generally drinkable food or drinkable consumer beverage products), the microbeads can generally be added to the finished drinkable consumer beverage product and optionally mixed in order to distribute the microbeads throughout the drinkable consumer beverage product. As discussed above, the microbeads are generally formulated such that they will not substantially break down in the drinkable consumer beverage product for a period of time. In this manner, the microbeads can be added to drinkable consumer beverage products during the normal manufacturing process and then distributed to retailers with the microbeads incorporated therein. Alternatively, the microbeads can be added to the drinkable consumer beverage product closer to the actual time of consumption, such as when a consumer adds the microbeads to a drinkable consumer beverage product just prior to consumption. In such embodiments, the microbeads can be provided in, for example, individual packets for easy storage and transport by the consumer.

With respect to food products having a generally solid consistency, the micobeads can be incorporated into the food products in any suitable manner. In some embodiments, the microbeads can be incorporated into the food product during the cooking, baking or general preparation of the food product. For example, when the food product is prepared by first preparing a batter or the like, the microbeads can be mixed in with the batter such that the microbeads are present in the product at the time the product if cooked, baked, or the like. In such embodiments, the microbeads can be formulated so as to resist higher cooking or baking temperatures without substantially breaking down. Microbeads can also be incorporated into a food product after a cooking or baking step.

Figure 4:
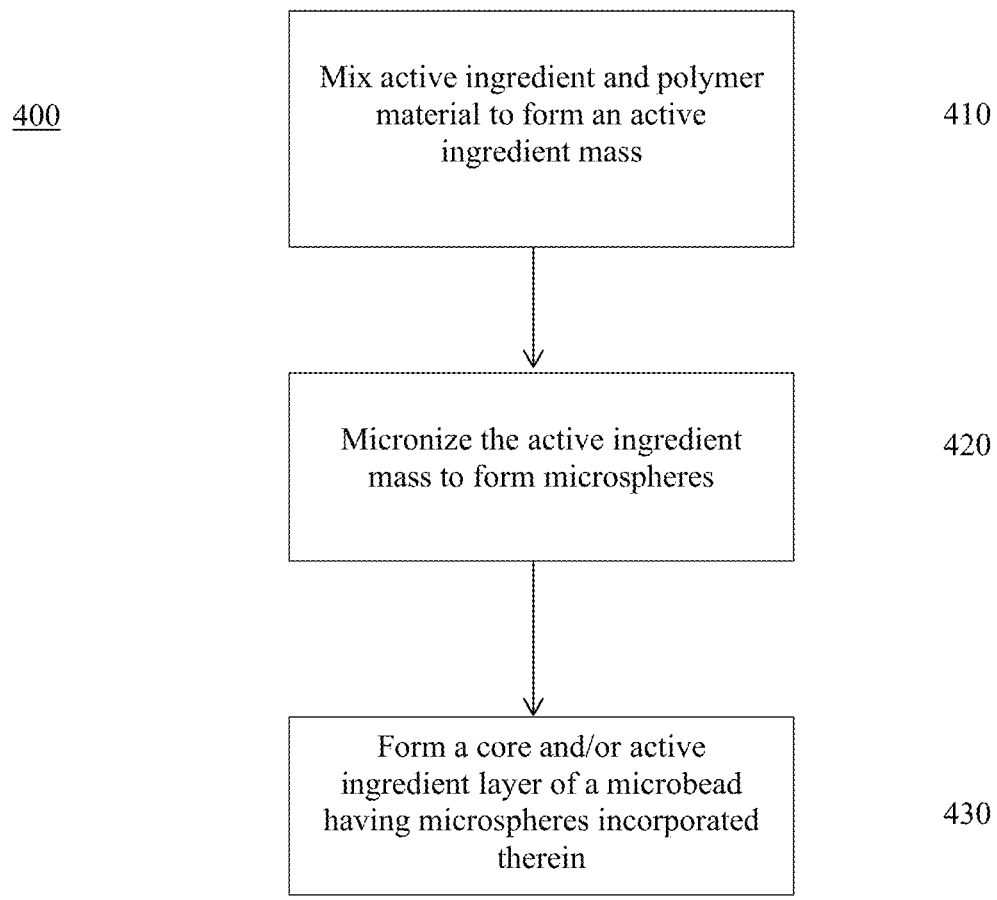
FIG. 4 is a flow diagram illustrating a method of forming layered microbeads according to various embodiments described herein.

With reference to FIG. 4, another method 400 that can be used in the preparation of a microbead core and/or one or more of the active ingredient layers is illustrated. The method generally includes a step 410 of mixing an active ingredient with a polymer to create an active ingredient mass, a step 420 of micronizing the active ingredient mass to form microspheres, and a step 430 of forming a core or an active ingredient layer having the microspheres incorporated therein.

In step 410, one or more active ingredients that are to be a part of the microbead are mixed with a polymer material to form a mass of polymer material having the active ingredient(s) dispersed therein. Any manner of mixing the active ingredient(s) and the polymer material can be used, provided that the active ingredient is dispersed throughout the polymer material.

In some embodiments, the amount of active ingredient in the mass is from 5% to 90% (based on the total weight of the active ingredient mass). In some embodiments, the amount of polymer in the mass is 10% to 95% (based on the total weight of the active ingredient mass). These ranges help to ensure that the active ingredient is present throughout the mass while also ensuring that the polymer material is covering the active ingredient material.

The active ingredients used in the forming the active ingredient mass can be any of the active ingredients listed above, including any combination of the above-listed active ingredients or classes of active ingredients. The polymers can be selected from the group including methyl cellulose, ethyl cellulose, microcrystalline cellulose, croscarmellose sodium, dicalcium phosphate, cellulose, hypromellose, hydroxypropyl methylcellulose, carboxymethylcellulose, hydroxyethyl cellulose, povidone, hypromellose, lipids/waxes, trigylcerides, phospholipids, carnuba wax, cottonseed oil, palm oil, soybean oil, and stearines.

Once the mass is prepared, it can generally be treated such that the mass is hardened. Any manner of hardening or solidifying the mass can be used. Exemplary methods include fluid bed drying, 3-D Printing, hardening solution bath, spray drying, and spray chilling.

In step 420, the solid mass is micronized to form microspheres. Any manner of micronizing the mass to form microspheres can be used. Similarly, any suitable apparatus for micronizing the mass can be used. In some embodiments, various parameters of the micronizing step can be altered to form microspheres of difference size and shape. Generally speaking, the microspheres formed have a diameter in the range of from 0.5 to 50 microns. Each microsphere formed from the micronizing generally includes a sphere of polymer material having active ingredient(s) dispersed throughout the polymer material. In some embodiments, the active ingredients in the microspheres are effectively coated by the polymer, which thereby creates a barrier that needs to be breached in order to access the active ingredient. In this manner, the microspheres can be used to further alter the sustained release nature of the microbeads into which the microspheres are incorporated.

In step 430, the microspheres can be incorporated into a microbead core, one or more active ingredient layers, or any combination thereof. The microspheres can be incorporated into the core by adding the microspheres with the active ingredient, binding agent, or other combination of ingredients used to form the core. Similarly, the microspheres can be incorporated into an active ingredient layer by adding the microspheres with the various components used in forming an active ingredient layer as described in greater detail above.

In some embodiments, the microspheres can be used in place of the active ingredients components discussed above with respect to the core and active ingredient layers. In such embodiments, the only active ingredient present in the core and/or active ingredient layers is the active ingredients present within the microspheres. Alternatively, the microspheres can be used in conjunction with active ingredient present in the cores or active ingredient layers.

EXAMPLES

Example 1

Rotary Granulation to Form Caffeine Core Bound with HPMC

A dry blend was prepared according to the following table:

TABLE 1

| Ingredient | Grade/Type | Dosage Wt. (mg) | % Dose Wt. | Batch Wt. (g) |
|---|---|---|---|---|
| Caffeine | Anhydrous 99% | 70 | 25 | 750 |
| Microcrystalline Cellulose | Avicel PH 101 | 126 | 45 | 1350 |
| Hydroxypropyl Methylcellulose | E5 | 42 | 15 | 450 |
| Sodium Chloride | Powdered | 42 | 15 | 450 |
| Total | | 280 | 100 | 3000 |

The mixture was deposited in a rotary granulator (model: Freund Vector VCF 3 with a GXR Insert) and air was applied into the chamber of the rotary granulator to blend the mixture and cause the mixture to become airborne. An interior temperature of 28° C. was achieved. The air was supplied at 90 psi and 12 cfm.

Water was subsequently sprayed into the rotary granulator using a variable speed peristaltic pump. The nozzle position for the sprayed water was tangential. The selected rotor disc had a smooth surface.

The overall process was carried out at the following parameters

TABLE 2

| | Process Time minutes | | | | | | |
|---|---|---|---|---|---|---|---|
| | 0 | 15 | 30 | 45 | 60 | 75 | 90 |
| Drying Airflow cfm | — | — | — | 50 | 50 | 50 | 50 |
| Slit Air cfm | 10 | 10 | 10 | 10 | 10 | 10 | 10 |
| Drying Accel Temp C. | — | — | — | 95 | 95 | 95 | 95 |
| Product Temp C. | 28 | 28 | 28 | 30 | 34 | 42 | 55 |
| Slit Air Temp C. | 50 | 50 | 50 | 50 | 50 | 50 | 50 |
| Exhaust Temp C. | 30 | 30 | 30 | 32 | 35 | 45 | 57 |
| Rotor Speed rpm | 400 | 400 | 400 | 400 | 400 | 400 | 400 |
| Spray Rate g/min | 40 | 40 | 40 | — | — | — | — |
| Nozzle Pressure psi | 10 | 10 | 10 | — | — | — | — |

Agglomeration of the material (and therefore core formation) began shortly after introduction of the water. The water began to saturate the airborne powder mix and interacting with the HPMC particles. While the cores grew, they also densified and spheronized via contact with the spinning rotor plate.

Once all of the water was consumed, drying air was activated for an additional 45 minutes until a product temperature of approximately 55° C. was achieved and dry microbead cores were formed.

Example 2

Spray Drying to Form Caffeine Cores

A solution was prepared according to the following table:

TABLE 3

| Ingredient | Grade/Type | Dosage Wt. (mg) | % Dose Wt. | Batch Wt. (g) |
|---|---|---|---|---|
| Caffeine | Anhydrous 99% | 85 | 85 | 425 |
| Hydroxypropyl Methylcellulose | E5 | 15 | 15 | 75 |
| | | 100 | 100 | 500 |

The solution was mixed using a variable speed mixer and a three-headed propeller in a suitable container. The solution was mixed until no solid particulates were observed.

The solution was subsequently sprayed into a spray dryer under the following parameters:

TABLE 4

| Spray Rate g/min | Inlet Temp C. | Outlet Temp C. | Spray Conc % |
|---|---|---|---|
| 30 | 160 | 80 | 10-40 |

Dried spherical microbead cores were produced having a particle size in the range of from 1 to 100 microns.

Example 3

Powder Layering Microbead Cores with Caffeine Active Ingredient Layer

Microbead cores were formed according to the method set forth in Example 1.

A binding solution containing 150 g of hydroxylpropyl methylcellulose (E5) was prepared.

The microbead cores from Example 1 were placed in the rotary granulator of Example 1 equipped with a powder layering nozzle attachment. Both nozzles positions were tangential.

The binding solution was sprayed through one nozzle concurrently with 540 g of caffeine sprayed through the second nozzle under the following parameters:

TABLE 5

| | Process Time minutes | | | | | | | | | |
|---|---|---|---|---|---|---|---|---|---|---|
| | 0 | 15 | 30 | 45 | 60 | 75 | 90 | 105 | 120 | 135 |
| Drying Airflow cfm | — | — | — | — | — | — | — | 50 | 50 | 50 |
| Slit Air cfm | 10 | 10 | 10 | 10 | 10 | 10 | 10 | 10 | 10 | 10 |
| Drying Accel Temp C. | — | — | — | — | — | — | — | 95 | 95 | 95 |
| Product Temp C. | 27 | 27 | 27 | 27 | 27 | 27 | 27 | 27 | 32 | 50 |

TABLE 5-continued

|  | Process Time minutes | | | | | | | | | |
|---|---|---|---|---|---|---|---|---|---|---|
|  | 0 | 15 | 30 | 45 | 60 | 75 | 90 | 105 | 120 | 135 |
| Slit Air Temp C. | 50 | 50 | 50 | 50 | 50 | 50 | 50 | 50 | 50 | 50 |
| Exhaust Temp C. | 31 | 31 | 31 | 31 | 31 | 31 | 31 | 31 | 35 | 54 |
| Rotor Speed rpm | 300 | 300 | 300 | 300 | 300 | 300 | 300 | 300 | 300 | 300 |
| Spray Rate g/min | 10 | 10 | 10 | 10 | 24 | 24 | 24 | — | — | — |
| Nozzle Pressure psi | 10 | 10 | 10 | 10 | 10 | 10 | 10 | — | — | — |
| Powder Feed g/min | 10 | 10 | 10 | 10 | 10 | — | — | — | — | — |
| Eductor Air | 14 | 14 | 14 | 14 | 14 | — | — | — | — | — |

Layering began shortly after the start of the spraying. Once the binding solution started to saturate the rotating microbead cores and interacting with the caffeine powder, growth of the active ingredient layer on the core began.

Once all of the caffeine powder was consumed, the binding solution became a functional coating, essentially sealing the layered microbeads.

Once all of the binding solution was consumed, drying air was activated for an additional 30 minutes until a product temperature of about 50° C. was achieved to dry the microbeads.

Example 4

Microbead Core-Encapsulating Layer Co-Extrusion Process

A microbead core solution was prepared using a carrier agent of sunflower oil combined with a pre-complexed active component of caffeic acid and caffeine. An encapsulating layer solution was prepared by heating carnuba palm wax to 95° C. The two solutions were then combined utilizing co-extrusion on a customized Buchi Encapsulator B-390 to manufacture microbeads having a core and an encapsulating layer. The microbeads were collected and allowed to cool in a collection bath reservoir of chilled ethanol. The encapsulation solution is comprised of the carnuba palm wax with the ethanol allowing for rapid cooling and hardening of the microbeads.

The overall process was carried out at the following parameters:

TABLE 6

| Nozzle System | Two Nozzle-Encapsulating Layer 300 μm, Core 200 μm |
|---|---|
| Flow Rate | 6 (Encapsulating Layer), 2 (Core) |
| Frequency | 600 Hz |
| Pressure | 0.5 Bar |
| Amp | 3 |
| Charge | >2000 V |

Example 5

Microbead Core-Dual Layer Tri-Extrusion Process

The core solution was prepared using a carrier agent of sunflower oil combined with a pre-complexed Ganeden BC-30® probiotic active ingredient (Nozzle 1). The intermediate layer solution was prepared by heating Stearine-07 nutrient/stabilizing blend to 60° C. (Nozzle 2). The outer encapsulating layer was prepared by heating Carnuba Palm wax to 95° C. (Nozzle 3). The three solutions were then combined utilizing tri-extrusion on a customized Buchi Encapsulator B-390 to manufacture the core-dual layered microbeads. The microbeads were collected and allowed to cool in a collection bath of ethanol.

The overall process was carried out at the following parameters

TABLE 7

| Nozzle System | Three Nozzle-Concentric-Outer Encapsulate 400 μm, Intermediate layer 300 μm, Core 200 μm |
|---|---|
| Flow Rate | 7 (Outer layer) 4 (Intermediate layer), 2 (Core) |
| Frequency | 4500 Hz |
| Pressure | 0.5 Bar |
| Amp | 3 |
| Charge | >1000 V |

Example 6

Microbead Core-Sealing Layer Layer 3-D Printing Process

A core dispersion/filament was prepared using an active ingredient of caffeine. A filament of polylactic acid was utilized for the sealing layer of the micro-bead. The two dispersions/filaments were then applied layer by layer using the 3-D system and software.

The overall process was carried out at the following parameters:

TABLE 8

| 3-D System | Utilimaker 2 |
|---|---|
| Sealing Filament | Polylactic Acid (PLA), Flexible White, 3.0 mm |
| Active Ingredient | Caffeine |
| Nozzle Temp | 230 degrees C. |
| Speed | 15 mm/sec |
| Bed Temp | 60 degrees C. |
| Resolution | 20 micron |

Example 7

Pre-Microbead Core-Micronizing Process

A micronized microsphere core mass was manufactured by melting wax, then adding an the active ingredient complex to the melted wax. This mass was dried in a fluid bed until completely dry. The dry mass was then micronized utilizing a Fitz-Mill instrument. The final micronized microspheres were added to polymers and sealing agents, and the mixtures were then used in a rotary granulation system to produce microbeads wherein the active ingredient layers and sealing layers include microspheres.

The overall process was carried out at the following parameters:

TABLE 9

| Rotary Granulator | Freund Vector VFC 3 with a GXR-35 Insert |
|---|---|
| Micronizing | Fitz-Mill |
| Active Ingredients | Caffeine and Theanine |

Microsphere inner particles were formed according to the method listed above.

A binding solution containing 150 g of hydroxylpropyl methylcellulose (E5) was prepared.

The microspere inner particles were placed in the rotary granulator of Example 1 equipped with a powder layering nozzle attachment. Both nozzles positions were tangential.

The binding solution was sprayed through one nozzle concurrently with 540 g of caffeine sprayed through the second nozzle under the following parameters:

TABLE 10

| | Process Time minutes | | | | | | | | | |
|---|---|---|---|---|---|---|---|---|---|---|
| | 0 | 15 | 30 | 45 | 60 | 75 | 90 | 105 | 120 | 135 |
| Drying Airflow cfm | — | — | — | — | — | — | — | 50 | 50 | 50 |
| Slit Air cfm | 10 | 10 | 10 | 10 | 10 | 10 | 10 | 10 | 10 | 10 |
| Drying Accel Temp C. | — | — | — | — | — | — | — | 95 | 95 | 95 |
| Product Temp C. | 27 | 27 | 27 | 27 | 27 | 27 | 27 | 27 | 32 | 50 |
| Slit Air Temp C. | 50 | 50 | 50 | 50 | 50 | 50 | 50 | 50 | 50 | 50 |
| Exhaust Temp C. | 31 | 31 | 31 | 31 | 31 | 31 | 31 | 31 | 35 | 54 |
| Rotor Speed rpm | 300 | 300 | 300 | 300 | 300 | 300 | 300 | 300 | 300 | 300 |
| Spray Rate g/min | 10 | 10 | 10 | 10 | 24 | 24 | 24 | — | — | — |
| Nozzle Pressure psi | 10 | 10 | 10 | 10 | 10 | 10 | 10 | — | — | — |
| Powder Feed g/min | 10 | 10 | 10 | 10 | 10 | — | — | — | — | — |
| Eductor Air | 14 | 14 | 14 | 14 | 14 | — | — | — | — | — |

Layering began shortly after the start of the spraying. Once the binding solution started to saturate the rotating microbead cores and interacting with the caffeine and theanine powder, growth of the active ingredient layers on the core began.

Once all of the caffeine and theanine powder was consumed, the binding solution became a functional coating, essentially sealing the layered microbeads.

Once all of the binding solution was consumed, drying air was activated for an additional 30 minutes until a product temperature of about 50° C. was achieved to dry the microbeads.

From the foregoing, it will be appreciated that specific embodiments of the invention have been described herein for purposes of illustration, but that various modifications may be made without deviating from the scope of the invention. Accordingly, the invention is not limited except as by the appended claims.

I claim:

1. A non-prescription consumable product, comprising:
    a layered microbead incorporated into the consumable product, the layered microbead comprising:
        a microbead core comprising:
            a first binding agent; and
            a plurality of first microspheres dispersed throughout the first binding agent, each first microsphere consisting of:
                a first active ingredient core consisting of a first active ingredient; and
                a first polymer encapsulating the first active ingredient core;
        a first active ingredient layer encapsulating the microbead core, the first active ingredient layer comprising:
            a second active ingredient;
            a second binding agent; and
            a plurality of second microspheres dispersed throughout the first active ingredient layer, wherein the second active ingredient is present in the first active ingredient layer outside of the plurality of second microspheres; and
        a second active ingredient layer encapsulating the first active ingredient layer, the second active ingredient layer comprising:
            a third active ingredient;
            a third binding agent; and
            a plurality of third microspheres dispersed throughout the second active ingredient layer;
    wherein the first active ingredient and the second active ingredient are non-prescription active ingredients.

2. The non-prescription consumable product of claim 1, wherein each second microsphere comprises:
    a second active ingredient core comprising a fourth active ingredient; and
    a second polymer encapsulating the second active ingredient core.

3. The non-prescription consumable product of claim 1, wherein the layered microbead has a diameter in the range of from 25 to 5000 microns and each microsphere of the plurality of first microspheres has a diameter in the range of from 0.5 to 100 microns.

4. The non-prescription consumable product of claim 1, wherein each of the plurality of second micro spheres has a diameter in the range of from 0.5 to 100 microns.

5. The non-prescription consumable product of claim 1, wherein the first active ingredient is a different active ingredient from the second active ingredient.

6. The non-prescription consumable product of claim 1, wherein the first active ingredient counteracts or reduces the effect of the second active ingredient.

7. The non-prescription consumable product of claim 1, wherein the first active ingredient enhances or complements the effect of the second active ingredient.

8. The non-prescription consumable product of claim 1, further comprising a sealing layer encapsulating the microbead core, the first active ingredient layer, and the second active ingredient layer.

9. The non-prescription consumable product of claim 8, wherein the sealing layer comprises a material or combination of materials that do not substantially break down in a food or drinkable consumer beverage product.

10. The non-prescription consumable product of claim 1, wherein the amount of second binding agent in the first active ingredient layer is different from the amount of third binding agent in the second active ingredient layer.

11. A non-prescription consumable product, comprising:
a layered microbead incorporated into the consumable product, the layered microbead comprising:
  a microbead core comprising:
    a first binding agent; and
    a plurality of first microspheres dispersed throughout the first binding agent, each first microsphere consisting of:
      a first active ingredient core consisting of a first active ingredient; and
      a first polymer encapsulating the first active ingredient core;
  at least one active ingredient layer encapsulating the microbead core, the active ingredient layer comprising:
    a second active ingredient;
    a second binding agent; and
    a plurality of second microspheres dispersed throughout the at least one active ingredient layer, wherein the second active ingredient is present in the at least one active ingredient layer outside of the plurality of second microspheres; and
  a first sealing layer disposed between the microbead core and the at least one active ingredient layer, wherein the first sealing layer encapsulates the microbead core, the at least one active ingredient layer encapsulates the first sealing layer, and the first sealing layer is free of active ingredients;
wherein the first active ingredient and the second active ingredient are non-prescription active ingredients.

12. The non-prescription consumable product recited in claim 11, wherein the first sealing layer does not substantially break down prior to being consumed.

13. The non-prescription consumable product recited in claim 11, wherein each second microsphere comprises:
  a second active ingredient core comprising a third active ingredient; and
  a second polymer encapsulating the second active ingredient core.

14. The non-prescription consumable product recited in claim 11, wherein the layered microbead has a diameter in the range of from 25 to 5000 microns and each microsphere of the plurality of first microspheres has a diameter in the range of from 0.5 to 100 microns.

15. The non-prescription consumable product recited in claim 11, wherein each of the plurality of second microspheres has a diameter in the range of from 0.5 to 100 microns.

16. The non-prescription consumable product recited in claim 11, wherein the first active ingredient is a different active ingredient from the second active ingredient.

17. The non-prescription consumable product recited in claim 11, wherein the first active ingredient counteracts or reduces the effect of the second active ingredient.

18. The non-prescription consumable product recited in claim 11, wherein the first active ingredient enhances or complements the effect of the second active ingredient.

19. The non-prescription consumable product recited in claim 11, further comprising a second sealing layer encapsulating the microbead core, the first sealing layer, and the at least one active ingredient layer.

* * * * *